United States Patent [19]

Ben-Simhon

[11] Patent Number: 5,085,657
[45] Date of Patent: Feb. 4, 1992

[54] ELECTROSURGICAL INSTRUMENT

[76] Inventor: Haim Ben-Simhon, 78-280 Mc Clelland Road, Nepean, Ontario, Canada, K2L 8P8

[21] Appl. No.: 594,704

[22] Filed: Oct. 9, 1990

Related U.S. Application Data

[63] Continuation of Ser. No. 341,956, Apr. 24, 1989, abandoned, which is a continuation of Ser. No. 475,145, Mar. 14, 1983, abandoned.

[51] Int. Cl.⁵ .............................................. A61B 17/39
[52] U.S. Cl. ........................................ 606/42; 606/45; 606/49; 604/35
[58] Field of Search ................ 606/41, 42, 45, 49; 604/22, 35

[56] References Cited

U.S. PATENT DOCUMENTS

| | | | |
|---|---|---|---|
| 2,029,487 | 2/1936 | Kleine | 606/49 X |
| 3,828,780 | 8/1974 | Morrison, Jr. | 606/49 X |
| 3,906,955 | 9/1975 | Roberts | 606/49 |
| 4,307,720 | 12/1981 | Weber, Jr. | 606/49 X |
| 4,445,517 | 5/1984 | Feild | 604/35 X |
| 4,516,398 | 5/1985 | Wuchinich | 604/35 X |
| 4,562,838 | 1/1986 | Walker | 604/35 X |
| 4,719,914 | 1/1988 | Johnson | 606/49 X |
| 4,919,129 | 4/1990 | Weber, Jr. et al. | 606/49 X |

FOREIGN PATENT DOCUMENTS 438420  1/1975  U.S.S.R. .................... 604/22

Primary Examiner—Lee S. Cohen
Attorney, Agent, or Firm—Martin J. Marcus

[57] ABSTRACT

A suction tube to be mounted on electro-cutting/coagulation apparatus and/or cutting/coagulation-suction apparatus and/or laser generated cutting/coagulation-suction apparatus for general and specific surgery usage. A cleaning mechanism is provided for removal of ash from blades of electro-cutting/coagulation apparatus, and/or laser generated cutting/coagulation apparatus. A flushing system is also included for removal of blood or debris from the suction tube.

13 Claims, 5 Drawing Sheets

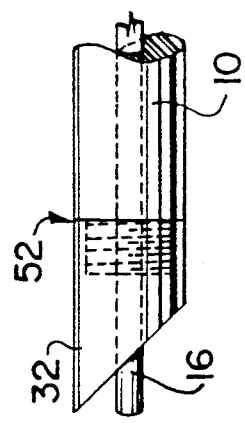
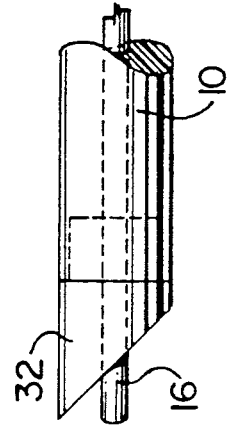
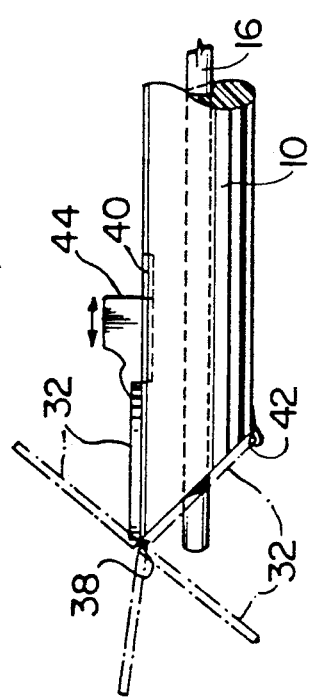
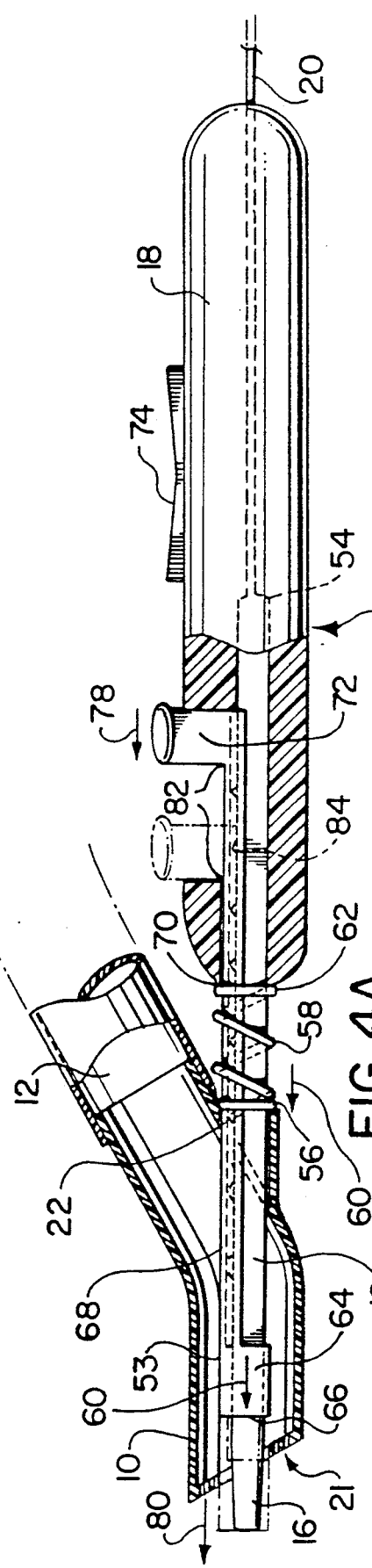
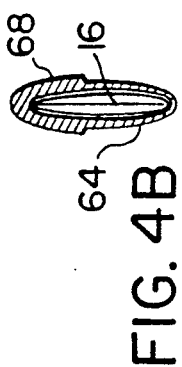

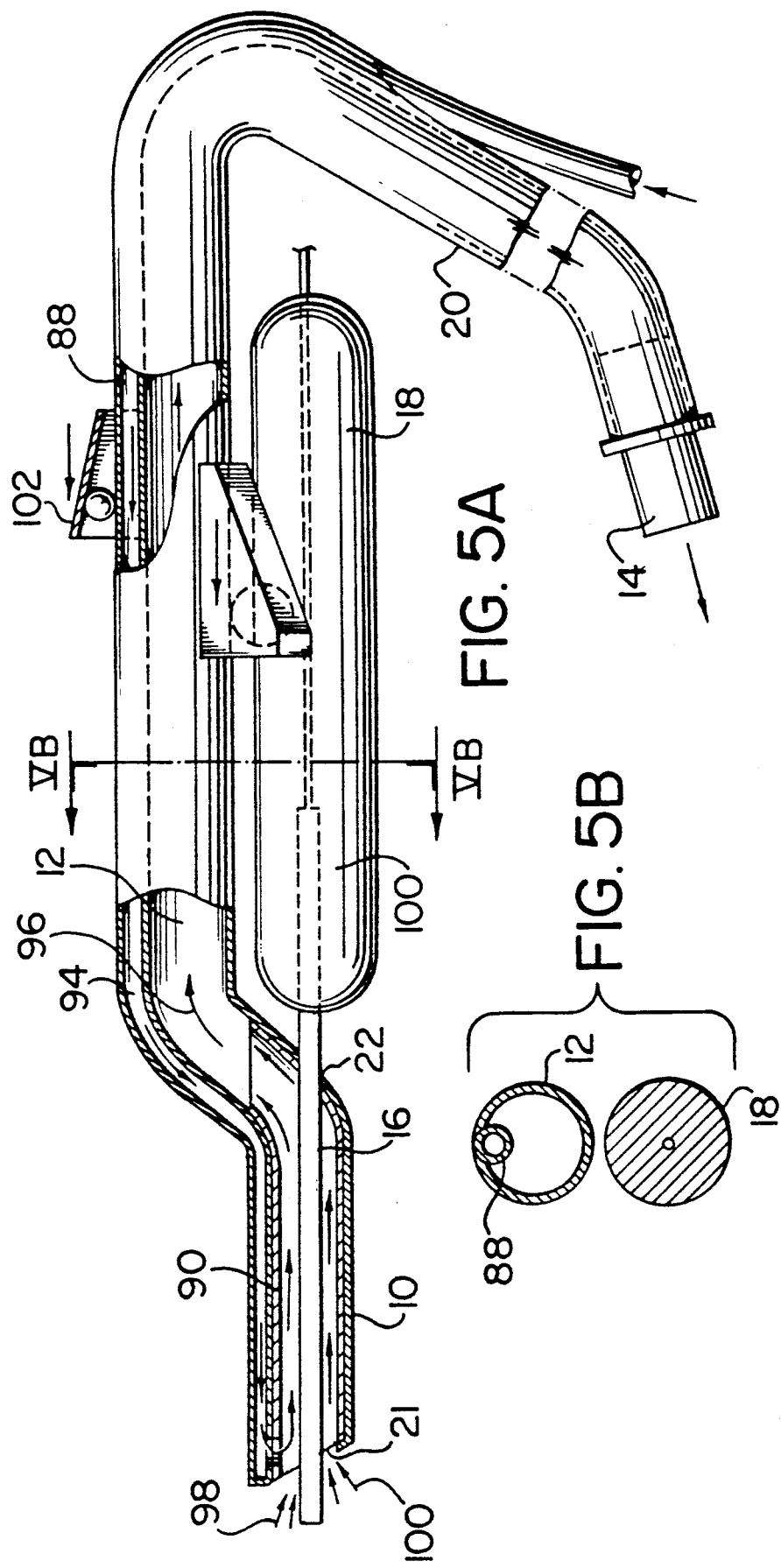

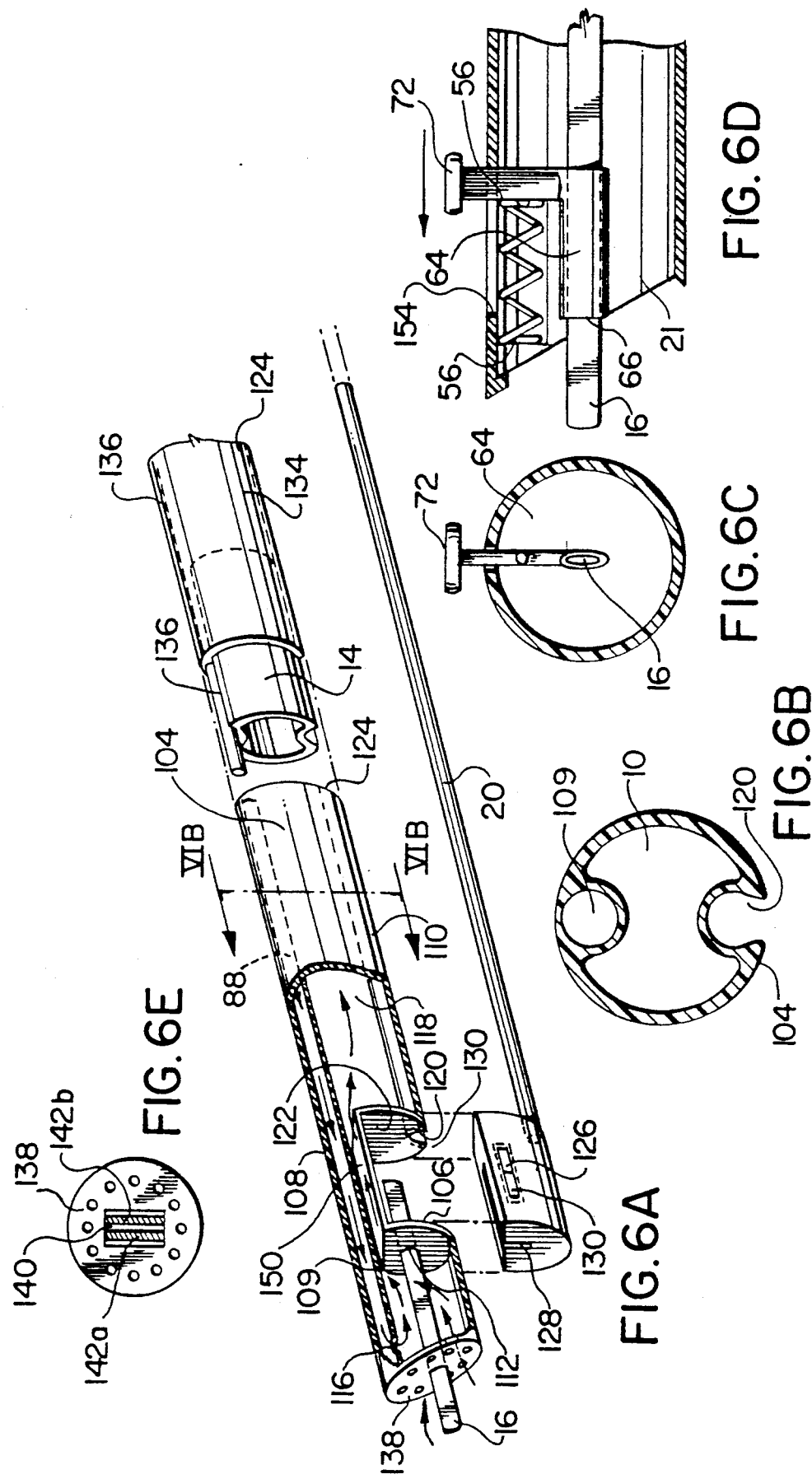

ELECTROSURGICAL INSTRUMENT

This is a continuation of application Ser. No. 341,956 filed Apr. 24, 1989, now abandoned, which, in turn is a continuation in part of application Ser. No. 475,145 filed Mar. 14, 1983, now abandoned.

The present invention relates to medical tools for general and specific surgery and more particularly to electro cutting/coagulation apparatus including a cleaning device for removal of ash formed in use.

BACKGROUND OF THE INVENTION

Almost every surgical procedure requires the use of electro-cutting or electro-cutting/coagulation apparatus. Cutting with an electric blade or laser blade creates irritating smoke, and cuts blood vessels which bleed. This bleeding in turn disturbs its proper action.

Inhaling the smoke is a health hazard similar to that of air pollution and cigarette smoking. Also, with the continuing exposure it has an accumulative detrimental effect on the lungs. Therefore, providing an electro-cutting instrument with the ability to remove a health hazard, is an advantage.

The first part of the invention is a specifically constructed tube that could be mounted and/or removed easily from existing forms of electric or laser scalpels. The invention is therefore also a combined cutting-coagulation-suction apparatus, and/or combined cutting-suction apparatus.

The advance made in the art of surgery is as follows: this suction tube, which is light-weight and can easily be mounted on an electric scalpel, removes the irritating smoke, which is usually inhaled by the surgeon and his staff, immediately after its formation. In fact, it removes the smoke simultaneously with the cutting and prevents it from being inhaled by the operating staff.

Inhaling the smoke is a health hazard similar to that of air pollution and cigarette smoking. Also, with the continuing exposure it has an accumulative detrimental effect on the lungs. Therefore giving an electro-cutting instrument the ability to remove a health hazard, is an advance to what exists so far.

Another advance is that it removes the blood simultaneously with the electro-cutting.

Usually, the blood that results from cutting covers the line of the cutting and also impairs the quality of the electro-cutting; thus the blood has to be removed before the electro-cutting can be continued.

In the course of the cutting or coagulation with an electric (or laser) blade, ash is formed and sticks to the cutting edge of the blade. This ash has to be scraped off to restore the normal function of the instrument. Usually the surgeon has to stop the course of the surgical procedure and clean the tip with another instrument.

SUMMARY OF THE INVENTION

The first part of the invention is a specifically constructed tube that could be mounted and/or removed easily from existing forms of electric or laser scalpels. The invention is therefore also a combined cutting-coagulation-suction apparatus, and/or combined cutting-suction apparatus.

The advance made in the art of surgery is as follows: this suction tube, which is lightweight and could easily be mounted on an electric scalpel, removes the irritating smoke, which is usually inhaled by the surgeon and his staff, immediately after its formation. In fact, it removes the smoke simultaneously with the cutting and prevents it from being inhaled by the operating staff. The idea of a simultaneous cutting-suction apparatus is original and new.

Another advance is that it removes the blood simultaneously with the electro-cutting (this applies also when it is mounted on a simple scalpel with a sharp edged blade). Removing the blood simultaneously with the cutting action spares the need to stop and wipe the blood or the need for an assistant for that purpose (the two actions are done by the surgeon who holds the combined instrument).

Another advance is that when mounted on an electric scalpel that is designed to also do coagulation, it sucks the blood from the surrounding of the cut-end of the vessel and enables proper coagulation of the bleeding vessel. Therefore, it constitutes a new instrument which combines three actions: namely, a cutting-coagulation-suction apparatus.

It is another purpose of this invention to free the surgeon from stopping the course of surgery for cleaning the instrument, and build a blade with a device that scrapes the ash from the tip by a single 1 cm move of the index finger tip of the hand which holds the instrument.

Because this is a very simple action, it could be performed during the course of procedure without stopping the main procedure. When this blade is mounted together with the suction device on the blade, the suction area will immediately suck the debris that is being scraped from the tip by the new device and prevent it from falling on the surgical field.

No such cleaning apparatus has been described and it is believed that the invention provides a new and useful device which constitutes an advance in the surgical armamentarium.

This device could be mounted in combination with the cutting-coagulation-suction apparatus and/or with a cutting-coagulation apparatus alone. More detailed explanation of the significance and place of this cleaning apparatus, is described in the disclosure of this application.

Another part of the invention is an optional infusion tube that is connected to the suction tube, and arranged to pour saline or sterile water into the suction tube in order to constantly flush the blood that might stick to the walls of the suction tube. Usually, the suction tubes do not block. However, in an especially long operation with an enlarged input of blood through the suction tube, the lumen of the suction tube could be narrowed by the clotted blood. The flushing will abolish this possibility completely. No flushing system in this constellation has been described and this also constitutes a new invention.

The invention could also be provided as a combined instrument: electro-cutting-coagulation-suction with flushing for the suction tube and cleaning for the electric blade.

BRIEF DESCRIPTION OF THE DRAWINGS

For a better understanding of the invention with regard to the embodiments thereof, reference is made to the accompanying drawings in which like numerals designate corresponding elements or sections throughout, and in which:

FIGS. 3a-c show, respectively, an optional perforated orifice plate for use with the suction tube of FIG. 1, a lock therefor, a cap-type of perforated plate, and a screw-cap type of perforated plate;

FIGS. 4a-b show, respectively, a cleaning device for the electro-cutting/coagulation scalpel handle of FIG. 1, and a cross-section thereof;

FIGS. 5a-b show, respectively, a flushing system for the electro-cutting/coagulation scalpel handle of FIG. 1, and a cross section thereof;

FIGS. 6a-e show, respectively, a scalpel handle having a tube in which all the cutting/coagulation-suction-flushing functions are included, a perforated plate for cleaning the blade, optional inverse construction of the tube, alternate perforated plate construction, and an optional cleaning tube.

DETAILED DESCRIPTION OF THE PREFERRED EMBODIMENTS

Figure 1:
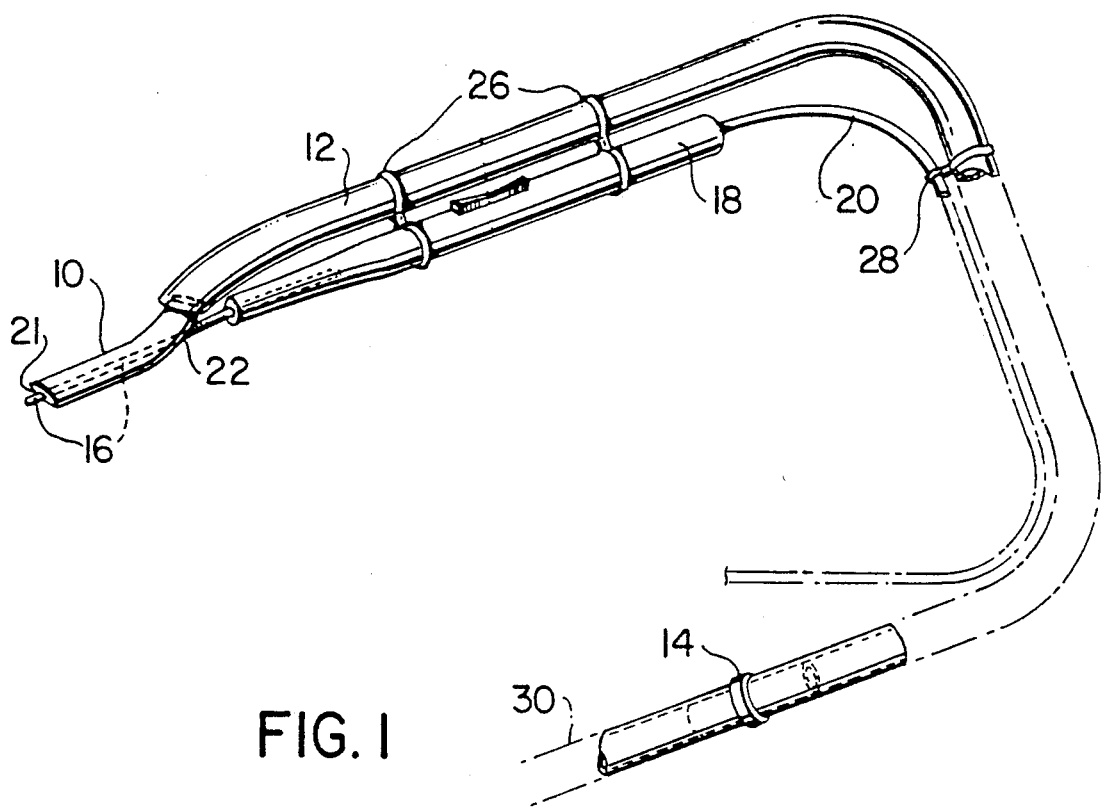
FIGS. 1 shows a preferred embodiment of a suction tube for an electro-cutting/coagulation scalpel handle, constructed and operated in accordance with the principles of the present invention.
Figure 7:
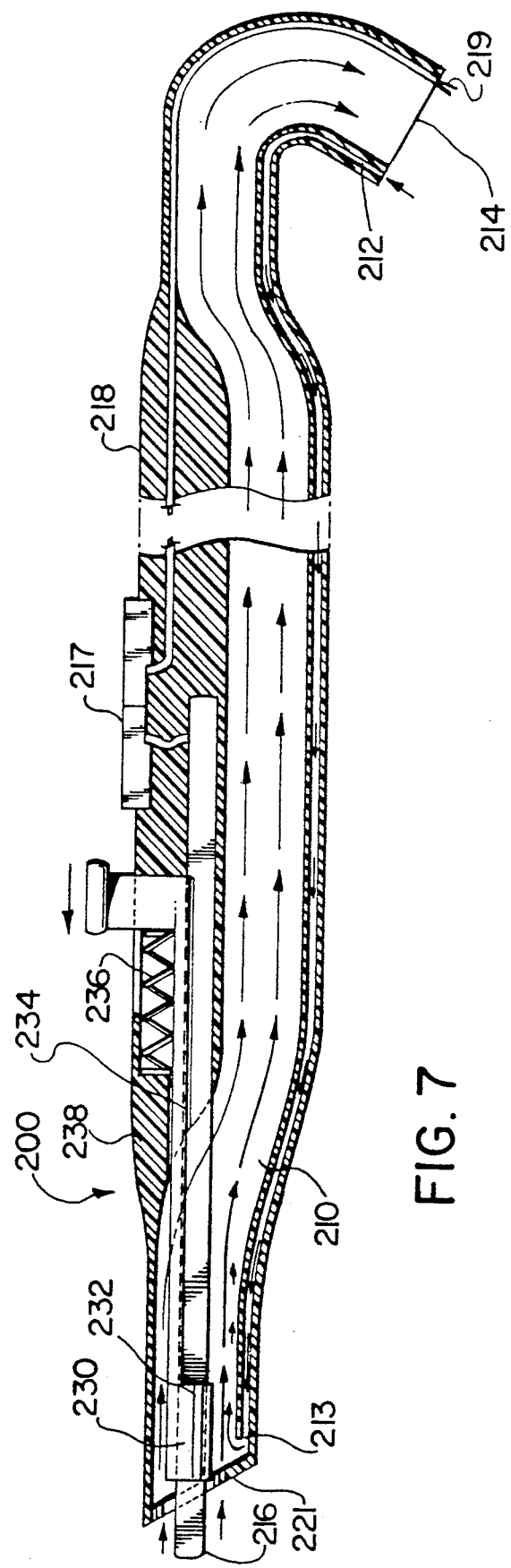
FIG. 7 is an alternative construction of the electro-cutting/ coagulation-suction apparatus of the invention.

The first part of the invention consists of six parts (tube 10, tube 12, connector 14, blade 16, scalpel handle 18, wire 20) attached to each other in the manner described in FIG. 1, and in FIG. 7. Tube 10 is the most important part and is made of hollow, round, hard transparent plastic tube, shaped in the form of a modified letter L, with an angle of 135° between the arms of the L. The horizontal arm is cut obliquely in a 45° angle to the plan of the horizontal arm to form an ellipse-shaped orifice 21. Through this orifice 21 the blade 16 of the electric scalpel 18 protrudes and approaches the tissue that is cut or the blood vessel that is coagulated. Through this orifice 21 the blood and smoke are sucked out of the tissue, to the inside of the tube 10. A vacuum generating apparatus attached to the tube 12 provides the suction.

The cutting blade 16 penetrates the horizontal arm of the modified L-shaped tube through an elliptoid slot 22 (in the form of the blade 16) in the conjunction between the two arms. The conjunction is especially thickened (see FIG. 2b) and the slot 22 is shaped exactly in the center of the tube 10, thus holding the penetrating blade 16 right at the center of the round lumen of the tube 10 and enables the blade 16 to protrude right in the center of the elliptogenic orifice 21. This arrangement is very important because it has two purposes:

(a) to provide a "suction area" to the cutting blade 16. This prevents "leaking" of the smoke which could result in incorrect placement of the blade 16.

(b) the protruding blade 16 prevents the tissue from being sucked into the tube 10, but allows the blood which is fluid and the smoke which is gas to be sucked into it.

Figure 2A:
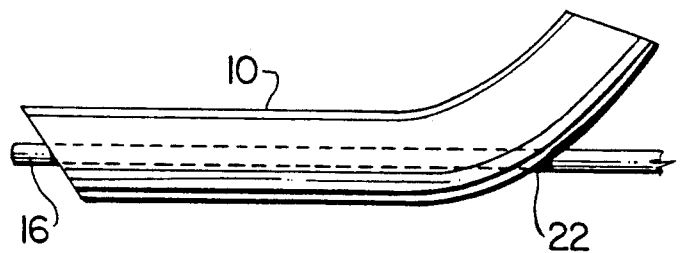
FIGS. 2a-b show, respectively, penetration of a scalpel blade through a slot in the suction tube of FIG. 1, and a cross-section thereof.
Figure 2B:
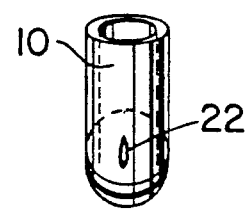

The back of the horizontal arm is formed with thickened plastic whose purpose is to give strength to the central positioning of the cutting blade 16 in the lumen of the horizontal arm. An enlarged drawing of this item is shown in FIG. 2b.

The elliptoid shape of the blade 16 and the slot 22 in the thickened "back" is to prevent rotation of the blade 16 inside the lumen of the horizontal arm and, of course, to prevent rotation of the protruding part of the blade 16. Prevention of rotation is important because when cutting, the sharper edge of the blade 16 has to be constantly opposite to the tissue that it cuts, otherwise the cut will not be sharp and straight.

The vertical arm of the modified L-shaped tube 10 is a continuation of the lumen of the horizontal arm; it serves as a connector to tube 12. (FIG. 1).

Tube 12 is a hollow round tube made from soft rubber or silicone. It is thin, lightweight and flexible. It is attached to the cutting scalpel 18 by two large plastic hooks 26 with an internal diameter the same as that of the cutting scalpel 18 handle, and with a shape as shown in FIG. 1. It has an outside tap to close the lumen of the tube 12, as an option (102 in FIG. 5a.

The hook consists of two rings: one is full and encircles the tube 12, and the other is not full and has two flexible arms with spring quality that enables the scalpel 18 handle to "pop in" by forcing it through the gap between the two spring-like arms. Along the tube 12 are other hooks 28 which are designed to hold the electric wire 20. These hooks 28 are the same as the hook 26, only with smaller arms or "open ring" to fit the smaller diameter of the wire 20. (FIG. 1).

The wire 20 is connected to the distal part of the scalpel 18 handle, and at the other end is connected to the cutting-coagulation generator.

The tube 12 is connected to another tube 30 by means of a plastic connector 14, and the latter tube 30 leads to a negative pressure generating apparatus that provides the suction power. The tube 12 is indirectly connected to the scalpel 18 through tube 10, which is connected to blade 16, which in turn is connected to scalpel 18.

The apparatus is used in the following manner: The surgeon holds the electric scalpel 18 with the tube 12 mounted thereon like one holds a pencil. Holding the scalpel 18 in this manner naturally creates an angle of about 45° between the instrument and the plan of work (which, like a piece of paper in the case of the pencil, is the tissue to be cut in the case of the surgical instrument). This natural angle is the reason for the oblique cross-section of the distal orifice 21 of tube 10 (at an angle of 45° to the horizontal arm of the modified L-shaped tube 10). Because the orifice 21 is cut obliquely at 45° the elliptoid surface lies parallel to cut-tissue underneath, when the instrument is held in the natural "pencil grasp", namely at 45° to the plan that is being cut.

Parallel orientation of the orifice 21 in relation to the field that is being cut is important because it enables an even suction of the blood and smoke from the field underneath and prevents smoke leakage. Together with the placement of the blade 16 in the center of the orifice 21, this construction enables an optimally efficient sucking of smoke and blood from the field, and therefore an optimal functioning of the apparatus. However, a round orifice 21 is another option of this invention and is used with increased negative pressures (FIG. 1b).

Another option and/or accessory is an elliptoid perforated (multiple perforations) plastic membrane 32 which could be mounted on the elliptoid orifice 21 of tube 10. (see FIG. 3). The membrane 32 will also have a slot 34 in its centre through which the electro cutting blade 16 could protrude.

This perforated membrane 32 could be attached firmly to the elliptoid orifice 21 causing a partial occlusion of the lumen (partial because of the perforations) and could be removed from the orifice 21, all at the surgeon's choice. This membrane 32 serves two purposes:

(a) because it partially occludes the orifice 21, it enables application of a milder negative pressure or suction power on the blood, smoke and tissue underneath, than without it (b) because it is firmly attached to the walls that form the orifice 21, and because of the central positioning of the slot 34 through which the blade 16 is protruding, it adds extra strength to the central positioning and fixation of the blade 16.

The importance of central positioning was described previously.

There are several ways to give the membrane 32 and/or cover, and/or cap the ability to occlude or to be removed from the orifice 21 at the surgeon's will. Examples of these are described as follows: A plastic perforated plate (membrane 32) that is attached to tube 10 in the upward pole of the elliptoid orifice 21 by means of a segment of soft plastic. This segment serves like a hinge around which the plate 32 can be rotated (point 38 in FIG. 3a, circular arrows showing direction of rotation). In fact, the plate 32 is an integral part of tube 10 (FIG. 3a). Tube 10 will have two plastic locks, one on top of the "roof" of the tube 10 (point 40 in FIG. 3a) and the other on the lower pole of the elliptoid orifice 21 (point 42 in FIG. 3a).

These plastic locks are designed to have a hook-shape which enables them to lock the plate 32, either parallel to the tube 10 by means of the lock in position 40 of FIG. 3b, or closing on the elliptoid orifice 21 by means of the lock in position 42 of FIG. 3b. Additional hook-locks may be placed on both sides of the elliptoid orifice 21 to add extra strength to the closure of the orifice 21, as an option of this invention.

The mode of operation of the lock is illustrated at 44 in FIG. 3a. Because the "arm" of the hook 46 is flexible, pressing the plate 32 toward the slope 50 will cause the edge of the plate 32 to engage the arm of hook 46.

Other possibilities of construction are a tight fitting cap like perforated plate 32, which is fitted to cover firmly the distal part of the tube 10 (FIG. 3c), or one that could be screwed over tube 10 on threads 52 (FIG. 3c). Both are options of this invention.

All three forms described above give the surgeon the possibility to open and/or close the orifice 21, as desired.

The cutting and/or coagulation, with electric or laser generated heat during surgical procedures, creates ash from the burnt tissue in the line of the cut or, from points that are coagulated. Part of this ash evaporates as smoke, another part sticks to the tissue that is being cut, and the greater part adheres to the part of the electric blade 16 that is in touch with the cut tissue. This latter part of ash forms an isolating barrier between the metallic blade 16 and the tissue it is supposed to cut. This barrier increases the resistance to the flow of current (and consequently of the heat) from the blade 16 to the tissue that is cut or coagulated, and consequently impairs the optimal cutting and/or coagulating function of the blade 16.

The amount of ash that adheres to the blade 16 is directly proportional to the amount of cutting or coagulating ("burning" in surgeons' slang) that is being performed. As the ash accumulates on the blade 16, resulting in a growing layer of ash formed thereon, the resistance to the flow of current becomes proportionately greater. This necessitates a longer application of the blade 16 on the tissue in order to achieve the same cut or coagulation that would have been achieved if the blade was clean from ash. Finally, the layer becomes so thick that no current flows to the tissue and it neither cuts nor coagulates and the surgeon has to make a break in the procedure and clean the blade 16 by means of scraping out the ash with a sharp metal blade or the blade of a scissors. This cleaning restores the conductance of the surface of the electric blade 16 and consequently, the proper flow of electric current from the blade 16 to the tissue is restored, thus achieving the proper cutting and coagulation functions of the instrument.

However, the steady increase in time needed for the cutting and/or coagulation, which finally leads to the inevitable arrest of the instrument function, and the inevitable necessity to stop the course of surgery and to clean the instrument, are two major disadvantages of the existing forms of electro-cutting blades.

Every major surgical procedure in the chest, abdomen (or limbs) includes, as the first stage of the operation, opening the chest or abdominal wall by cutting through its layers. The main instrument used in this stage of the operation is the electro-cutting-coagulation scalpel by which the different layers are cut by the main surgeon. The assistant in this stage holds a separate suction apparatus and/or sponges and wipes the blood.

The process of cutting through the layers by the primary surgeon consists of cutting with the electro-cutting instrument and when a considerably-sized blood vessel is cut and needs to be coagulated, the main surgeon presses on the coagulation button and the electric blade 16 coagulates (of course, he has to wipe out or clean the blood as explained before). Thus, the process is one of alternating operations of cutting and coagulation by the same blade 16 (only by presssing on different buttons—each button releases current which results in the respective operation, namely suction or coagulation).

Now, both operations, suction and/or coagulation contribute ash that clings to the blade 16 as explained before. Cleaning the blade 16 constitutes a break and/or deviation from the "natural" course of the operation, namely, cutting and coagulation and thus comsumes time and interferes with the practicability of the procedure.

It will be appreciated that building a blade 16 with an "auto cleaning" mechanism which is easy to operate by a 1 cm push of a small lever by the index finger that holds the instrument is very desireable. The cleaning device 53 (FIG. 4a of this invention includes a blade 16 stretched from its protruding tip to the connection with the scalpel handle at point 54. The blade 16 enters the lumen of the horizontal arm of tube 10 through a slot 22 in the thickened wall of the vertical arm of the tube 10 just prior to its entrance blade 16 has two slightly raised holding points which prevent the spring 58 that encircles the blade 16 from moving forward when the spring is pushed in the direction of the arrow 60 by the slightly different diameter ring 62. Ring 62 is an integral part of the body of the cleaning device 53. The cleaning device itself is a 1 cm long hollow metal tube 64 that has the same cross section as blade 16, only very slightly larger, to allow the blade 16 to fill the lumen of this elliptoid cleaning tube 64 (see FIG. 4b). This tube 64 has a razor sharp leading edge 66 which lies very closed to the blade 16 it encircles (the size of the gap 67 between them is just big enough to allow sliding of the tube 64 long the tip of the blade 16).

The tube 64 is connected in its upper wall to a metallic sem-circular strip 68 which is in fact an integral part of tube 64 (see FIG. 4b). The semi-circular strip 68 lies over the upper part of blade 16, and "runs" along, parallel and adjacent to blade 16. This strip 68 can slide over the blade 16, and it comes out of the plastic tube 10 also in slot 22, at the back of the vertical arm of tube 10. At one point, it has—as an integral part in a ring—ring 62, which encircles the blade 16 and can slide over it. Because ring 62 has a "rim" like a "doughnut" that covers the last ring of the spring 58, it can push and compress spring 58 if pushed in the direction of arrow 60. (Note two enlargements (holding points 56) in the blade 16 that prevent the sp ring 58 from "running" forward). On the other hand, the compressed spring 58 can push ring 62 back by its stored energy.

The semi-circular strip 68 enters the scalpel 18 handle at point 70 and ends in a lever-shaped edge 72 that bulges out of the handle of the scalpel 18 near the on/off knob 74. The scalpel 18 is held like a pencil, i.e. the index finger pushes on knob 74 and the thumb on point 76. The mode of operation is as follows: the surgeon by this index finger pushes the lever 72 one (1) cm in the direction of arrow 78. This results in a movement of 1 cm of the strip 68, of which lever 72 is an integral part. The movement of the strip 68 in the direction of arrow 78 (forward) pushes the tube 64 with its sharp leading edge 66 in the same direction (arrow 80), namely forward. The moving sharp edge 66 which lies intimately on the blade 16 shaves the debris from the tip of the blade 16 that was in touch with the burnt tissue and on which the ash accumlated (the ash accumlates only on the part that touches the cut tissue). In other words, the 1 cm move causes the leading edge 66 to pass over the tip of blade 16, shaving and pushing the debris off the blade 16, where the debris "meets" the suction area provided by tube 10. In other words, the negative pressure in the elliptoid orifice 21 area of tube 10 sucks the debris (like a vacuum cleaner) in the direction towards tube 12 and prevents it from falling on the surgical field. Simultaneously, the pushing of the lever 72 causes compression of the spring 58 in the direction of arrow 60. Thus, the spring 58 is squeezed between ring 62 and the holding points 56 on the blade 16, which results in increasing the stored energy of the spring providing a retrieving mechanism.

Now, when the surgeon releases his index fingertip from the lever 72, the spring 58 pushes the whole device 53 with the cleaning tube 64 backwards to the resting position. This releases the tip of the blade 16 that was covered by tube 64 when the spring 58 was compressed (when cleaning device 53 is in the active position) and now the tip is clean and ready for action again.

The great advantage of this arrangement is that the easy operation (fingertip movement) will encourage the surgeon to clean the edge more frequently (he does not have to make a break in the flow of the procedure) and thus keep the blade 16 constantly at its optimal quality (no debris, no increased resistance to the flow of the electric current). This will have a significant contribution to the fluency of the surgical procedure.

Other possibilities of placing the retrieving mechanism of the device 53 include: placing the spring 58 around the semi-circular strip in segment 82, thus hiding it inside the scalpel 18 handle, or placing the holding point 56 of blade 16 in point 84, the "doughnut" ring 62 of the semi-circular strip 68 in point 86 of the semi-circular strip 68 and the spring 58 encircling the blade 16 between point 84 and 86. This will also hide the retrieving part inside the scalpel 18 handle. A similar cleaning device 53 mounted on bipolar forceps coagulation and-/or bipolar coagulation suction apparatus is an option of this invention.

The infusion tube portion of the invention consists of the following: an infusion tube 88 (see FIG. 5a) which runs parallel to the suction tube 12. In fact, tube 10 and 12 are provided as a double lumen tube, the small diameter lumen is for the flow of flushing fluid and the large diameter is the suction tube itself. (See cross section in FIG. 5b). Tube 88 is connected to tube 10 through connector 90 in one end and on the other end it is connected to an infusion fluid bag.

The flow of the fluid in the tube 88 is caused by hydrostatic pressure which results from placing the infusion bag on a level higher than the level of connector 90. The rate of flow is regulated by means of a plastic tap which controls the width of the lumen of the tube 88 and is placed close to the connection of the tube 88 with the fluid bag or bottle or on the part close to tube 12. (Part 92 in FIG. 5a). Connector 90 has a hollow lumen and is an integral part of tube 12.

The mode of operation is as follows: the flushing fluids is constantly flowing in the direction of arrow 94 in tube 88 (due to the hydrostatic pressure) and flows into tube 10 through the connector 90 (nozzle). The fluid spreads inside tube 10, and since there is a constant suction area in tube 10, it is immediately sucked in the direction of arrow 96, flushing the wall of the tube 10 from blood or debris. Note that the flushing fluid cannot leak either through the elliptogenic orifice 21 or through the slight gap that exist in slot 22 in the rear. This is due to the existence of air movement towards the tube 10 in both points (arrows 98 and 100) that is caused by the constant negative pressure inside tube 10. It is clear that connector 90 can be placed in any point along tube 10 or 12.

The continuing whistle resulting from the continuous suction through the tube 10 is annoying to some surgeons. This is abolished by placing an intravenous infusion type tap on tube 12 that could narrow and close the lumen of the tube 12 by turning the wheel of the device 102 in FIG. 5a.

An alternative embodiment of this invention of cutting/coagulation-suction-flushing apparatus is "cancelling" the scalpel 18 handle (see FIG. 1) and arranging the suction tube 12 and flusing (infusion) tube 88 in the position of the handle. The idea is to have one tube which will include all functions of the apparatus, namely isolated connection to the electric wire 20 and off/on knob 74, the suction tube (10 and 12), and the flushing tube 88. FIGS. 6a–d illustrated the invention.

The tube 104 is formed of round, transparent plastic with a semi-cylindrical depression 106 towards the frontal edge of the tube 104; thus, the tube 104 consists of an oblique or round orifice followed by a hollow cylinder which continues as a semi-cylindrical lumen in the segment 108 of the depression 106 and the continue as a hollow round tube. The semi-circular plastic plate 109 that constitutes the "back" of the frontal cylinder 110 has an elliptoid hole 112 through which the electric blade 16 could be inserted in and/or out.

In the upper part of the tube 104, the flushing tube 88 is provided as a second small tube in which the flushing fluid flows and pours into the lumen of tube 104 near the orifice at point 116. In the lower wall of the posterior cylinder 118 of tube 104, there is a longitudinal groove 120 which is elastic and designed to house the electric cord 20. Note that the groove 120 starts in the posterior wall of the depression (in plate 122) and ends at the back of the tube 104 in point 124. However, it is an option to continue the groove in the following tube that is connected by connector 14.

The electric unit 126 is made from plastic in a semicylindrical shape, similar to the shape of the depression 106. It is made in one piece with the electric cord 20 and is completely isolated except in point 128 where it is designed to grasp the posterior edge of blade 16. The unit 126 had an off/on apparatus and knob on its side 130. The apparatus at point 128 that grasps the blade 16 in the unit 126 is a conventional apparatus and had four metal strips in a circular arrangement that spread forcefully when the blade 16, which has a larger diameter than that formed by the cross-section of the metal strips, penetrates between them when mounted on the unit 126.

The unit 126 fits exactly in the depression 106 in tube 104, and is kept in place by the blade 16 that penetrates the unit 126 in front and by the cord 20 in the groove 120 in the back. Plate 109 is especially thickened to add extra strength for holding the blade 16 and the unit 126.

Note that because of the suction area there will be no leakage from the hole 112 on plate 109 through which the blade 16 exists the tube 104. The connection in the rear is as follows: Tube 104 connects to another tube 134 through connector 14, and this in turn leads to the vacuum generating apparatus. Cord 20 remains as one unit until it connects to the electro-cutting generator, this to maximize isolation of the current. The flushing tube 88 connects to the infusion tube 136 through a regular connector.

Note the arrows showing fluid flowing in tube 88, pouring through point 116 and being sucked in the opposite direction in tube 104.

In another alternative embodiment of this invention, a rotatable, lock-hooked, perforated plate 138 with a slot 140 for the blade 16 is provided similar to that described in FIG. 3a. However, in this embodiment there is a modification that enables the rotating plate 138 to clean the blade 16 from accumulating ash. The slot 140 has two sharp razor pieces 142a–b in both sides of the slot 140, incorporated firmly into the plastic plate 138 (see FIG. 6e). When the plate 138 is rotated downward towards the orifice, blade 16 has to penetrate the slot 140. Since the slot 140 is very narrow, the razors 142a–b shave and push the debris inward to tube 104, where they are sucked away by the existing vacuum (arrows in FIG. 6a).

The mode of operation with this instrument is as follows: first, the electric unit 126 is inserted into the depression 106, the cord 20 is inserted in the groove 120 of tube 104, then the blade 16 is inserted through the orifice 21 and through the hole 112 in plate 109 to the "blade grasper" at point 128, which is part of the electric unit 126. The on/off knob 130 is on the right side of the instrument and is activated by the index finger of the hand which grasps the instrument like a pencil.

A modification of this invention is a cleaning tube 64 encircling the blade 16 that has sharp edges 66 (FIG. 6d) and a lever 72 that extends outside the top of tube 104 through slot 154. Another modification of this invention is a retrieving mechanism as in FIG. 4 a, provided with holding points 56 in FIG. 6d.

The objective of the invention is to unite all the different operations in one tube.

Further, it is the objective of the invention to give the surgeon a practical, handy electro-cutting apparatus which is provided with an assisting suction tube and flushing capability for the suction tube. The apparatus is grasped like one grasps a pencil, and is thus easy to manipulate while doing the main procedures of cutting and coagulating.

Note the protruding of the blade 16 from the orifice 21 of tube 104, which enables cutting and coagulation in a suction environment.

In conclusion, the four parts of the disclosure describe different aspects of a major surgical instrument: the electro-cutting-coagulation apparatus. Note that many combinations are possible in constructing the instrument, and these include:
  (a) Electro-cutting-coagulation-suction apparatus.
  (b) Electro-cutting-coagulation with built-in cleaning mechanism.
  (c) Combination of (a) and (b).
  (d) Electro-cutting-coagulation-suction apparatus with flushing system of the suction tube.
  (e) The combination that includes all the options namely: Electro-cutting-coagulation-suction apparatus with a built-in cleaning system for electric blade and built-in flushing system for suction tube.

It is important to note that this device has a primary function to cut and coagulate. The secondary actions of the suction, flushing and cleaning of the blade are only to assist or to clear the way for the fluent execution of the main function, namely cutting and coagulation and this whole combination as such constitutes a new original concept of the mode of operating the cutting-coagulation apparatus in surgical procedures.

Alternatively as shown in FIG. 7 an electro cutting instrument, similar to that of FIG. 5, shown generally as 200 includes the suction cleaning cauterizing and cutting functions all combined within a handle 218 of the instrument. The instrument 200 has an electrode blade 216 having an inner end connected to two position switch means 217 (to cut or cauterize) which is in turn connected to a source of R.F. energy through a supply wire 219.

A suction channel 210 having an orifice 221 adjacent the tip of blade 216, surrounds the blade 216 and extends under the handle 218. The suction channel 210 becomes a tube 212 at the trailing end of the handle where it is either formed of flexible plastic or is joined to flexible supply tubing by a connector at 214. A second and smaller channel and supply tube 213 provides flushing fluid to the first channel 210 adjacent the orifice 221.

The cleaning means 230 of this embodiment is a cylindrical member 232 carried by the blade 216 adjacent its forward end. The cylindrical member is similar to that of FIG. 4b and therefore need not be described in detail. A member 234 interconnects the cylindrical member 232 and a manually engagable portion 234 which extends out of the handle adjacent the switch assembly 217, a helical compression spring 236 is interposed between the manually engagable portion 232 and stop means 238 provided in the handle of the instrument 200. The spring is compressed when the cleaning element is moved forward and returns the cleaning element to a stored position when released.

It will be appreciated that when in use as described above, suction is available at the tip of the instrument to remove smoke, blood and ash and that the suction tube is cleaned by fluid drawn in from the fluid supply tube 213. The surgeon also has fingertip control of the blade cleaning element so that cutting and cauterizing can continue without delays previously encountered in such surgical procedures.

I claim:

1. The combination of:
   A) a cutting-coagulation scalpel including a handle, an electrical lead to said handle, switch means on said handle, a blade electrode mounted at one end of said handle and connected to said electrical lead through said switch means on said handle for selectively activating and deactivating said blade electrode for cutting action or for coagulation action; and
   B) a suction tube removably mounted on said handle, said suction tube being connectable to a source of suction and comprising a modified L-shaped hard plastic transparent tube having a longitudinal arm and an angular arm, with an angle of 135° between said longitudinal arm and said angular arm, said longitudinal arm having an open end and a back end, and being provided, at said open end, with an orifice, and, at said back end, with a thickened wall having a slot therethrough allowing penetration of said blade electrode therethrough, a soft plastic tube, said angular arm being connected to said soft plastic tube, said soft plastic tube having a first set of hooks thereon, said first set of hooks each comprising two rings, one ring completely encircling said soft plastic tube, the other ring being constituted by two flexible arms to allow said handle to pop in between a gap between said two flexible arms thereby allowing said ring to be mounted on, and being positively attached to, said handle, and having a further set of hooks thereon for holding only said electric lead, each of said further set of hooks having a closed ring encircling said soft tube and an open ring, said open ring being formed by two flexible arms, each of said further set of hooks being sized to allow said electrical lead of said cutting-coagulation scalpel to be engaged and disengaged in it, said blade electrode penetrating said modified L-shaped tube through said slot in said back end of said longitudinal arm, and being held in the center thereof by said thickened wall and protruding out of said orifice so that said blade electrode approaches cut and coagulated tissue area, and a tap disposed on said suction tube, said tap being selectively operable to connect said suction tube to said source of suction, or to disconnect said suction tube from said source of suction.

2. The combination as claimed in claim 1 further comprising a cleaning device for said blade electrode, said blade electrode cleaning device comprising: a metallic scraper element including a cylinder-like tip, said tip having razor-sharp edges encircling said blade electrode and having a slightly larger cross-section than said blade electrode, said tip being slidable on said blade electrode, said blade electrode having two slightly raised holding points thereon and being fixed to said scalpel handle and said slot in the back end of said modified L-shaped tube, a spring encircling said blade electrode around a portion of said blade electrode between said one end of said handle and said holding points and being retained behind said holding points; an actuating lever on said blade electrode, metallic strip connecting said tip and said lever, a portion of said strip being slidable with respect to a portion of said blade electrode, said strip being integrally formed, at one end thereof, with said cylinder-like tip; whereby, when said lever is pushed towards said tip, it causes sliding of said tip in close proximity to said blade electrode thereby to scrape said blade electrode and causing compression of said spring, and, when said lever is released, said tip is restored to its initial position by spring energy.

3. An electrosurgical instrument comprising: an insulated housing, a blade electrode mounted at one end of said housing; an electrical unit including switch means for selectively activating and deactivating said blade electrode, said electrical unit being disposed in said insulated housing; a suction channel having an orifice adjacent a tip of said blade electrode; a second channel operatively connected to said suction channel for conveying flushing fluid to said suction channel; scraping cleaning means for scraping said blade electrode carried by said blade electrode, said scraping cleaning means including manual operable means for urging said scraping cleaning means to a forward position, said manual operable means operating against spring means which urge said scraping cleaning means to a retracted, stored position, whereby release of said manual operable means allows said spring means to urge said scraping cleaning means from its forward position to its retracted stored position.

4. An electrosurgical instrument as claimed in claim 3 wherein said switch means is a two position switch for controlling cutting and coagulation procedures.

5. An electrosurgical instrument as claimed in claim 3 wherein said switch means is provided on said housing.

6. An electrosurgical instrument comprising:
   a) a handle having a forward end and a rear end;
   b) a suction tube having a forward end, a rear end, and side walls, connected to said handle, said rear end of said suction tube being adapted to be connected to a source of suction, and said forward end of said suction tube projecting beyond the forward end of said handle, said suction tube including an aperture in a side wall of the forward end thereof; the forward end of said suction tube being flattened to an ellipsoidal cross-section in a region where it surrounds a blade electrode, the forward end of said suction tube terminating in a distal obliquely-slanted outer face, and including an elliptically-shaped perforated membrane secured to said aperture, said membrane including a slot through which said blade electrode protrudes;
   c) an electrical lead extending into said handle from said rear end thereof;
   d) a blade electrode, having a forward end and a rear end, said rear end of said blade electrode being secured to the forward end of said handle, and being in electrical connection to said electrical lead, and said forward end of said blade electrode projecting through said aperture in said side wall of said forward end of said suction tube, and projecting beyond said forward end of said suction tube, said blade electrode being completely surrounded by said suction tube; and
   e) a switch connected between said electrical lead and said blade electrode for selectively activating and deactivating said blade electrode.

7. The electrosurgical instrument of claim 6 including a thin, lightweight, flexible tube of soft rubber or silicone, the rear end of said suction tube being connected to said thin lightweight flexible tube, said thin lightweight flexible tube being adapted to be connected to a source of suction, said thin lightweight flexible tube having sufficient resiliency to allow flexibility at the rear end of said handle for ensuring convenient manipulation of said instrument.

8. An electrosurgical instrument comprising:
   a) a handle having a forward end and a rear end and having a longitudinal axis;
   b) a suction tube having a forward end, a rear end, and sidewalls, connected to said handle, said rear end of said suction tube being adapted to be connected to a source of suction, said forward end of said suction tube projecting beyond the forward end of said handle, and extending along an imaginary extension of said longitudinal axis of said handle, said suction tube including an aperture in a side wall of the forward end thereof;
   c) an electrical lead extending into said handle from said rear end thereof;
   d) a blade electrode having a forward end, an intermediate portion and a rear end, a top edge of said rear end of said blade electrode being secured to the forward end of said handle, and being in electrical connection to said electrical lead, said intermediate portion of said blade electrode being disposed through said aperture in said side wall of said suction tube, said aperture being operatively associated with a rearwardly-extending ledge, said blade electrode being supported on said rearwardly-extending ledge, the forward end of said blade electrode projecting beyond the forward end of said suction tube, said blade electrode being completely surrounded by said suction tube;
   e) a switch connected between said electrical lead and said blade electrode for selectively activating and deactivating said blade electrode; and
   f) scraper cleaner means for scraping said blade electrode and slidably mounted on said blade electrode, and manually movable means for moving said scraper cleaner means from an inactive position to a forward position in scraping sliding contact with said blade electrode, and back to said inactive position.

9. The electrosurgical instrument of claim 8 including a thin, lightweight, flexible tube of soft rubber or silicone, the rear end of said suction tube being connected to said thin, lightweight, flexible tube, said thin, lightweight, flexible tube being adapted to be connected to a source of suction, said thin, lightweight, flexible tube having sufficient resiliency to allow flexibility at the rear end of said handle for ensuring convenient manipulation of said instrument.

10. The electrosurgical instrument of claim 8 wherein said handle includes a longitudinally-extending slot within which said scraper cleaner means is adapted to slide, said scraper cleaner means comprising:
   (i) a scraper member having the same cross-section as said blade electrode but being just slightly larger thereof;
   (ii) a rearwardly-extending connecting member enveloping said top edge of said blade electrode and extending into said longitudinally-extending slot in said handle;
   (iii) a lever integral with, and upstanding from, said rearwardly-extending connecting member and slidable in said longitudinally-extending slot; and
   (iv) a coil spring encircling a portion of said blade electrode, said coil spring being disposed between the forward end of said handle and a rear edge of said rearwardly-extending ledge.

11. The electrosurgical device of claim 9 wherein said handle includes a longitudinally-extending slot within which scraper cleaner means is adapted to slide, said scraper cleaner means comprising:
   (i) a scraper member having the same cross-section as said blade electrode but being just slightly larger thereof;
   (ii) a rearwardly-extending connecting member enveloping said top edge of said blade electrode and extending into said longitudinally-extending slot in said handle;
   (iii) a lever integral with and upstanding from said rearwardly-extending connecting member and slidable in said longitudinally-extending slot; and
   (iv) a coil spring disposed in said longitudinally extending slot, one end of said spring abutting a wall of said longitudinally-extending slot, the other end of said spring abutting said lever.

12. The electrosurgical instrument of claim 8 including an infusion tube only adapted to be connected to a source of flushing fluid, said infusion tube having a rear end, a forward end, and a side wall, and running parallel to, and in contact with, said suction tube, said rear end of said infusion tube being connected to a source of flushing fluid, and said forward end of said infusion tube being provided with an aperture in said side wall thereof connecting with an aligned aperture in an adjacent side wall of said suction tube.

13. The electrosurgical device of claim 12 wherein said handle includes a longitudinally-extending slot within which said scraper cleaner means is adapted to slide, said scraper cleaner means comprising:
   (i) a scraper member having the same cross-section as said blade electrode but being just slightly larger thereof;
   (ii) a rearwardly-extending connecting member enveloping said top edge of said blade electrode and extending into said handle; longitudinally-extending slot in said handle;
   (iii) a lever integral with, and upstanding from, said rearwardly-extending connecting member and slidable in said longitudinally-extending slot; and
   (iv) a coil spring disposed in said longitudinally-extending slot, one end of said spring abutting an end wall of said longitudinally-extending slot, the other end of said spring abutting said lever.

* * * * *